United States Patent [19]

Pierce

[11] Patent Number: 4,551,431
[45] Date of Patent: Nov. 5, 1985

[54] THE USE OF GALLIUM AND INDIUM SALTS FOR THE IMMOBILIZATION OF PROTEINS

[75] Inventor: Phyllis J. Pierce, Bartlesville, Okla.

[73] Assignee: Phillips Petroleum Company, Bartlesville, Okla.

[21] Appl. No.: 487,362

[22] Filed: Apr. 21, 1983

[51] Int. Cl.[4] .................... C12N 11/14; A61K 37/16; A61K 37/48
[52] U.S. Cl. .................................. 435/176; 424/94; 424/131; 514/6
[58] Field of Search ................ 435/176; 424/157, 156, 424/94, 131; 514/6

[56] References Cited

U.S. PATENT DOCUMENTS

| | | |
|---|---|---|
| 2,125,553 | 8/1938 | Winegarden et al. ............... 424/157 |
| 2,364,579 | 12/1944 | Wyckoff .............................. 424/157 |
| 3,016,336 | 1/1962 | Scott et al. . |
| 3,250,596 | 5/1966 | Grafe .................................... 424/89 |
| 3,329,564 | 7/1967 | Aguiar et al. ........................ 424/156 |
| 3,850,751 | 11/1974 | Messing . |
| 3,912,593 | 10/1975 | Barker et al. . |
| 3,982,997 | 9/1976 | Eaton et al. . |
| 3,983,000 | 9/1976 | Messing . |
| 4,002,576 | 1/1977 | Gregory et al. .................... 435/176 |
| 4,115,198 | 9/1978 | Coughlin et al. ................... 435/176 |
| 4,127,385 | 11/1978 | Weeke ................................ 424/1.1 |
| 4,193,910 | 3/1980 | Rohrbach et al. . |
| 4,194,066 | 3/1980 | Kaetsu et al. . |
| 4,450,233 | 5/1984 | Mimura et al. . |

FOREIGN PATENT DOCUMENTS

| | | |
|---|---|---|
| 0100660 | 2/1984 | European Pat. Off. . |
| 59-11185 | 1/1984 | Japan . |

OTHER PUBLICATIONS

Aiba et al., *Biochemical Engineering*, 2nd Ed. (Academic Press, N.Y. 1973), Chapter 14, "Immobilized Enzymes", pp. 393-417.
Baratti et al., *Biotech. & Bioengol.*, vol. XX, #3, Mar. 1978, pp. 333-348, "Preparation and Properties of Immobilized Methanol Oxidase".
*Chemical & Engineering News*, "Enzymes Technology", *C&EN*, Aug. 18, 1975, vol. 53, No. 33, pp. 22-41.
Goldstein et al., "Immobilized Enzymes-A Survey", *Applied Biochemistry and Bioengineering*, vol. 1, Immobilized Enzyme Principles (Academic Press, N.Y. 1976), pp. 1-59.
Goldstein et al., "The Chemistry of Enzyme Immobilization", *Appl. Biochem. & Bioeng.*, vol. 1, Wingard, Katchalski-Katzir and Goldstein, Ed. (Academic Press, N.Y. 1976) pp. 96, 97, 110, 111, 118 and 119.
Gray et al., "Immobilized Enzymes in Analytical Chemistry", *Analytical Chemistry*, vol. 49, No. 12, Oct. 1977, pp. 1067A, 1069A, 1070A, 1073A, 1074A, 1076A & 1078A.
Gulberg et al., "The Use of Immobilized Alcohol Oxidase in the Continuous Flow Determination of Ethanol with an Oxygen Electrode", *Analytica Chimica Acta*, 123 (1981), pp. 125-133.
Hartmeier, "Basic Trials on Possible Industrial Applications of an Immobilized Glucoseoxidase-Catalase System", *C.A.* 90, 119744u (1979).
Johnson et al., "On the Use of Polymerizing Gel Systems for the Immobilization of Trypsin", *J. Colloid & Interface Science*, vol. 37, No. 3, Nov. 1971, pp. 557-563.
Messing, *Immobilized Enzymes for Industrial Reactors*, (Academic Press, NY 1975), pp. 1-10 and 63-71.
Mosbach, Editor, *Methods in Enzymology*, vol. XLIV, "Immobilized Enzymes" (Academic Press, N.Y. 1976), pp. 652-658.
Royer, "Immobilized Enzymes Catalysis Reviews, 1978", *Catal. Rev.-Sci. Eng.*, 22(1), pp. 29-73 (1980).
White et al., "Reviews Popular Matrices for Enzyme and Other Immobilizations", *Enzym. & Microbialtech.* 2, #2, pp. 82-90.
Zaborsky, "Enzymes: Biological Catalysts", *Adv. Materials & Catalysis*, J. Burton and R. Garten, Eds. (Academic Press 1977), pp. 267-291.

*Primary Examiner*—Sam Rosen
*Attorney, Agent, or Firm*—Lyell H. Carver

[57] ABSTRACT

A dry, stable, particulate hydrous gel/protein composite prepared by coprecipitating by alkaline treatment a hydrous aluminum, gallium, or indium gel, and a protein, separating, and drying such as precipitating an aluminum hydroxide gel and an enzyme and drying. The dried composite can be ground and sized.

25 Claims, No Drawings

THE USE OF GALLIUM AND INDIUM SALTS FOR THE IMMOBILIZATION OF PROTEINS

The invention pertains to the immobilization of proteins. In a particular aspect, the invention pertains to the immobilization of enzymes.

BACKGROUND OF THE INVENTION

The term "proteins" includes a number of physiologically active and chemically active materials, including enzymes, cofactors, and cofactor analogs.

Many of these materials, but particularly the enzymes, exhibit the capability of promoting many different types of reactions, such as stereospecific reductions, oxidations, isomerizations, specific degradations, complex syntheses, and the like. Unlike most conventional inorganic catalysts, the protein-type substances generally are relatively water-soluble and may be relatively unstable, frequently being usable only once in aqueous solution as a free-component. Economical use of such may depend upon availability of means for recovery, recycling, and regeneration of relatively costly proteinaceous components.

Thus, it can be advantageous to immobilize the protein substance, which then permits multiple or repetitive use of a single quantity of enzyme or other protein, and provides the ability to stop a reaction rapidly by removing the active protein from the reaction solution or vice-versa. In many cases, an enzyme is stabilized in the immobilized form has a much longer active life. The solution containing the components being processed is not contaminated with the protein, thus decreasing separation requirements. For analytical purposes in particular, these protein substances, particularly enzymes, exhibit long half-life, thus reducing reagent preparations.

A variety of immobilization techniques have been proposed in recent years, such as crosslinking without benefit of carrier, crosslinking within carriers or on the surfaces of carriers, covalent attachment to carriers, adsorption on or in carriers, and encapsulation or entrapment.

U.S. Pat. No. 3,912,593 has taught, as one method, the mixing of a nitrogen-containing substance with a hydrous oxide or hydrous hydroxide of a metal such as tin, iron, vanadium, titanium, or zirconium, in an aqueous medium to form a solid metal chelate of the nitrogen-containing substance, and including the formation thereof in situ. However, I have found that the particular hydrous materials taught therein are not necessarily satisfactory. Improvement in reliability clearly has been needed.

BRIEF SUMMARY OF THE INVENTION

I have discovered that the use of a hydrous oxide or hydroxide selected from aluminum, gallium, or indium, of Group IIIA, prepared in situ, achieves effective incorporation of the active protein, such as an enzyme, into the hydrous metal oxide or hydroxide.

The incorporation of the active protein, such as an enzyme, is obtained by the slow addition of an aqueous solution of a water-soluble Group IIIA metal salt, selected from among aluminum, gallium, and indium, preferably aluminum, to a solution or dispersion of the protein while simultaneously adding an alkaline solution such that the pH of the dispersion is maintained at a level suitable for the coprecipitation of the protein and the metal oxide or hydroxide and suitable for the stability of the protein. The resulting hydrous gel/protein is separated and dried, and can be ground to a suitable particle size.

The resulting product is useful, stable, highly active, and possesses a long shelf-life. Comparisons with similarly prepared oxides or hydroxides from zinc, a Group IIB metal, show the superiority of my compositions and techniques. Comparison with a hydroxide of iron, a Group VIII metal, again shows the superiority of my product and technique.

So far as I can determine, no one heretofore has prepared a dry powdered uniform composite metal oxide gel/protein using aluminum, gallium, or indium of Group IIIA of the Periodic Table, by simultaneous precipitation of gel and protein, followed by drying. The product is active, water-insoluble, has long storage life, and is easily and conveniently measured, dispensed, and used. It is indeed surprising that the ultimate dried composite of protein retains a high activity despite the relatively severe and rough treatment involved in its preparation and isolation.

DETAILED DESCRIPTION OF THE INVENTION

In accordance with my invention, (a) a solution or dispersion of the desired active protein, such as of an enzyme, is formed in water, preferably in distilled or deionized water. Specific examples of protein substances include enzymes such as alcohol oxidase, catalase, glucose oxidase, glucose isomerase, lactase, invertase, $\alpha$- and $\beta$-amylase, pullulanase, penicillin acylase, bacterial protease trypsin, chymotrypsin, glucoamylase, dextranase, glucosidase, and Maxatase TM ; lectins such as concanavalin; hormone releasing factors such as follicle stimulating hormone releasing factor, luteinizing hormone releasing factor, and adrenocorticotropic hormone; hormones (proteins) such as follicle stimulating hormone and luteinizing hormone; antibodies in antipneumococcus sera and various $\gamma$-globulins; and antibiotics such as penicillin, gramidicin D, lathumycin derived from the microorganism *S. lathumensis*, neomycin, polymyxin, streptomycin, ampicillin, and chloroamphenicol; co-enzymes such as nicotinamide adenine dinucleotide (NAD) and reduced nicotinamide adenine dinucleotide (NADH); whole cells such as baker's yeast, *Escherichia coli, Pichia pastoris,* and the like.

The Group IIIA metal gels in accordance with my invention are formed from suitable water-soluble metal salts of certain members of Group IIIA of the Periodic Table, specifically of aluminum, gallium, or indium. The aluminum salts are preferred because of availability and ease of handling.

To this (a) aqueous solution or dispersion of the protein substance in water is simultaneously added with stirring (b) a dilute aqueous solution of the Group IIIA metal salt, and (c) a strongly alkaline aqueous solution containing a dilute solution of a Group IA alkali metal or ammonium hydroxide, preferably sodium hydroxide or ammonium hydroxide, sufficient to maintain the pH of the stirred (a-b-c) admixture in a range effective for coprecipitation of the Group IIIA hydrous metal oxide or hydroxide and protein.

My procedure produces a suspension of a coprecipitated relatively uniform composite of the Group IIIA hydrous metal oxide or hydroxide and the protein. This hydrous gel/protein is separated such as by centrifuging, filtering, or the like. The wet substance is dried to form a dried generally granular composite. The dried composite can be sized as covenient for various purposes such as catalytic usages.

The metal salts that are employable in the context of my invention are the water-soluble salts of aluminum, gallium, or of indium, presently preferred are the aluminum salts, such as the nitrate, acetate, chloride, bromide, and the like. For maximal biological activity, mixing of the nitrogen-containing organic substance, the alkaline solution, and the metal salt should be done in the substantial absence of carbon dioxide, carbonates, bicarbonates and chelating ions (e.g. citrate) which can chelate the metal ion and chelation of the nitrogen-containing organic substance adversely modify the nature of the hydrous metal oxide or hydroxide.

The aqueous solution of the Group IIIA metal salt should be made up to a strength of about 1 to 10 weight percent of the metal salt, preferably in the range of about 3 to 8 weight percent, although it is contemplated that, if desired, concentrations of the metal salts up to saturation concentrations can be used.

The strongly alkaline reagent is an aqueous ammonium or Group IA alkali metal hydroxide solution, presently preferred being aqueous sodium hydroxide for convenience and economy in large-scale usages. The alkaline solution can be of varying concentration, simply employing more of a dilute solution and less for stronger solutions, but conveniently a strength of about 0.1 to 1N is suitable, although aqueous sodium hydroxide solutions of up to 50 weight percent can be used.

In accordance with my process and procedure to make the immobilized protein, a protein-containing solution is made up to contain in the broad range of about 50 to 5000 enzyme units/mL, more usually in the range of about 200 to 4000 enzyme units/mL.

To the (a) protein-containing solution or dispersion is then added, substantially simultaneously, (b) a dilute solution of about 1 to 10 weight percent of the metal salt, and (c) the alkaline solution. The simultaneous addition of the metal salt solution, and of the pH-adjusting agent, results in the formation of a gelatinous precipitate of the metal as the hydrous metal oxide or hydroxide with the protein or proteins. The reactants are introduced, of course, with sufficiently gentle agitation of the aqueous mixture to permit the coprecipitation and adsorption of the hydrous metal oxide and protein, without excessively shearing or breaking up of the resulting gel-like product.

Thereafter, excess aqueous liquor is removed such as by vacuum stripping, freeze-drying, centrifugation followed by decantation, filtration, and the like.

The thus-isolated gel-like reaction mass preferably is washed with distilled water until the washings are substantially free of dissolved electrolytes.

The washed hydrous gel matrix then is dried, e.g., in vacuo at ambient temperature, or at a temperature of about 40° C. to 70° C. in a conventional drying oven, preferably with air circulation.

The resulting product is a dry immobilized-protein uniformly dispersed in and protected in the dry gel matrix. It can be further ground and sieved for size uniformity as desired without damage to the protein or any significant loss of activity.

It should be noted that neither the aqueous metal salt solution nor the alkaline solution should be added alone, or before the other, to the protein solution, to avoid possibly damaging effects on the protein, such as coagulation or denaturation.

A particular advantage of my invention is that various additives can be readily admixed into the protein (e.g., enzyme) preparation. For example, stabilizers such as sodium azide can be admixed in the aqueous protein solution/dispersion, and become part of the precipitated gel. Colorants can be similarly employed, thus colour-coding the gel. Mixtures of enzymes in specific ratios can be employed, resulting in stable specific ratios in the dried protein gel matrix.

I hereinafter describe the technique and product of my invention in terms of the use of an enzyme, more particularly of an alcohol oxidase enzyme. However, I wish it to be understood that the use thereof in the working Examples is to assist one skilled in the art to a further understanding of my invention, without limiting my invention merely to enzymes or to enzymes of the particular species so employed. Thus, the runs in the examples are discussed in terms of a *Pichia pastoris*-derived alcohol oxidase. This is employed for exemplary purposes, however, it is a highly active and presently preferred alcohol oxidase.

The presently preferred alcohol oxidase is obtained from methanol utilizing Pichia-type microorganisms comprising microorganisms of genus Pichia and microorganisms genetically and/or taxonomically closely related to Pichia. Specific examples of such methanol-utilizing Pichia yeast include: *Pichia pastoris, Pichia pinus, Pichia trehalophila,* and *Pichia molischiana*.

Alcohol oxidase can be obtained commercially from chemical and biological supply houses. However, in a preferred embodiment the alcohol oxidase is obtained from fermentation of an alcohol by a selected microorganism followed by separation of the alcohol oxidase.

An alcohol oxidase (alcohol: oxygen oxidoreductase) can be isolated from *Pichia pastoris* in soluble form, or crystallized to purity, using a dialysis precipitation procedure. Such a yeast contains about 20 percent of its total protein as alcohol oxidase. The enzyme can be isolated from a suspension of cells taken from a fermentor by homogenizing in a Dynomill glass-bead mill and separating the resultant supernatant containing the alcohol oxidase from the cellular debris by centrifugation. This supernatant, containing about 200–300 enzyme units (eu) per mL, can be further treated by adjusting the pH to 6.5 and dialyzing against 10 volumes of water. When the molar ionic strength of the crude enzyme solution suitably decreases, a precipitate of the alcohol oxidase forms. The precipitate contains over 80 percent of the enzyme units formerly present in the supernatant and is approximately 95 percent pure alcohol oxidase.

The above supernatant with relatively high enzymatic activity from *Pichia pastoris* (200–300 eu/mL) also contains large amounts of catalase, an enzyme which rapidly dismutates two moles of hydrogen peroxide into one mole of oxygen gas and two moles of water. Thus, alcohol oxidase is obtainable from *Pichia pastoris* in various degrees of purity:

(a) Whole single cell protein suspension: Both alcohol oxidase and catalase enzymes are available over long time periods by diffusion through cell walls.
(b) Homogenate of ruptured cells: Both alcohol oxidase and catalase enzymes are available in solution with significant amounts of cellular debris.
(c) Supernatant after centrifugation of (b): The cell-free supernatant contains relatively high enzymatic activity (200–300 eu/mL) comprising alcohol oxidase and catalase.

(d) High purity alcohol oxidase by dialysis of (c): The precipitated alcohol oxidase of about 95 percent purity accounts for over 80 percent of the enzymatic activity of the above supernatant.

Broadly, according to a preferred method of preparing the alcohol oxidase, an aqueous suspension of cells having alcohol oxidase activity is prepared by fermentation of methanol as carbon energy substrate using a methanol-utilizing microorganism. This aqueous suspension of cells, hereinafter referred to as "alcohol oxidase preparation I" or "AOPI," exhibits alcohol oxidase activity over a relatively long period of time by diffusion thereof through the cell walls.

The aqueous suspension of cells can be homogenized to produce a homogenate, referred to as "alcohol oxidase preparation II" or "AOPII", having alcohol oxidase activity.

Suspended solids can be removed from such a homogenate by centrifugation, filtration, or the like, and the resulting supernatant or cell-free fluid can be used as a crude solution, referred to as "alcohol oxidase preparation III" or "AOPIII", having alcohol oxidase activity.

A crystalline, electrophoretically pure alcohol oxidase, referred to as "alcohol oxidase preparation IV" or "AOPIV", can be further prepared from "AOPIII" by ultrafiltration or dialysis or by other suitable means, presently preferably and conveniently by dialysis.

In a number of applications wherein $H_2O_2$ by-product is considered undesirable, it is desirable that the enzyme catalase also be present.

The net effect of the reactions catalyzed by the enzyme combination of alcohol oxidase and catalase is the effective scavenging of free oxygen and the conversion of the by-product $H_2O_2$ into water.

Alcohol oxidase preparations "AOPI", "AOPII", and "AOPIII" each have substantial catalase activity so that additional catalase need not be added when combined alcohol oxidase and catalase activity in accordance with the invention is required.

Crystalline alcohol oxidase, "AOPIV", however, is substantially free of catalase activity and is the preferred preparation where the presence of $H_2O_2$ is not undesirable. Alternatively, of course, catalase or some other suitable enzyme such as peroxidase can be added to the "AOPIV" if such is desirable.

EXAMPLES

Examples provided are intended to assist a further understanding of my invention. Particular species employed, conditions, and the like, should be considered as exemplary, and not limitative of the reasonable scope of my invention as disclosed in the specification including the Examples and claims.

Alcohol Oxidase Preparation: Isolation

The cell-free supernatant of alcohol oxidase for use in the Examples of my invention was isolated from the fermentor effluent from an aqueous aerobic fermentation process employing a Pichia-type yeast, more particularly a *Pichia pastoris* species, operated under aqueous aerobic fermentation conditions employing methanol as carbon energy substrate. The resulting yeast cells were separated from the aqueous ferment by centrifugation.

The cell-free supernatant of alcohol oxidase for use in the present invention was isolated from the fermentor effluent. The effluent was adjusted to a pH of about 7.5 and homogenized at a high cell density concentration such as 100–120 grams biomass (dry weight)/liter using a Dynomill TM Model KDL using a 0.6 liter vessel in a continuous operation at 5° C. to 30° C. using belt combination #3 and a flow of 20–30 mL/hr. The homogenate solids were separated by centrifugation to give a cell-free aqueous supernatant containing alcohol oxidase, catalase, and other soluble proteins. This supernatant contained on the order of 200–300 eu/mL wherein an enzyme unit is that amount of enzyme necessary to convert 1 micromole of methyl alcohol to one micromole of formaldehyde per minute.

The electrophoretically pure crystalline alcohol oxidase was obtained by dialysis of the cell-free supernatant. The crude solution containing the soluble alcohol oxidase was dialyzed against a dialysis medium across a membrane impermeable to alcohol oxidase but permeable to water, buffer, and inorganic molecules. The type of membrane used is not considered critical. For example, commercially available cellulose acetate dialysis tubing can be used to form dialysis bags, or hollow fiber dialysis cells can be used. The alcohol oxidase containing solution can be dialyzed against a dialysis medium, for example water or a buffer solution, to achieve a recovery range solution on the enzyme side of the membrane having an ionic strength in a recovery range of between 0.05M and 0.01M thereby effecting precipitation of an electrophoretically homogeneous crystalline alcohol oxidase.

Alternatively, the fermentor effluent containing whole cells can be treated by my method to obtain an immobilized whole cell enzyme-containing system useful, for example, for promoting the removal of dissolved oxygen from aqueous alcohol solutions. The homogenate containing cellular debris can be similarly processed in accordance with my invention to obtain additional immobilized enzyme-containing systems useful, for example, for promoting the removal of dissolved oxygen from water-alcohol mixtures.

EXAMPLE I

This run demonstrates the effectiveness of an aluminum hydroxide gel immobilized alcohol oxidase system to promote the removal of dissolved oxygen from an aqueous methanol solution. The immobilized alcohol oxidase system was prepared by contacting cell-free supernatant (as hereinabove defined) with aluminum nitrate solution using aqueous sodium hydroxide to maintain the pH in the range of about 6 to 7.

A 450 mL sample of "PHS" ("Pichia homogenate supernatant") was placed in a 1-liter beaker equipped with a magnetic stir bar and pH meter. The "PHS" sample contained approximately 371 enzyme units (eu) per mL (total 450 mL sample activity of 167,000 eu) (no sodium azide). A sample of aqueous aluminum nitrate solution [66 g $Al(NO_3)_3 \cdot 9H_2O/550$ mL $H_2O$](176 mmoles $Al^{+3}$) was placed in a separatory funnel and added drop-wise to the stirred aqueous mixture containing alcohol oxidase, catalase, and other water soluble proteins. During this addition, the pH of the mixture was monitored and maintained in the pH range of about 6.6–7.1 by the drop-wise addition of aqueous sodium hydroxide solution (40 g NaOH/1 liter $H_2O$). Precipitation was continuous throughout the period of aluminum nitrate addition and the final pH reading was about 6.9.

The precipitate was removed by suction filtration with a fritted glass Buchner funnel and washed repeatedly with deionized water giving a clear yellow-colored filtrate. The air-dried precipitate weighed about 48 grams. The 48 g sample was ground in a mortar with a pestle to give a pulverized solid. This solid gave about 31.8 grams of solid which passed a #10 size mesh screen but not a #20 size mesh screen.

A 20 g sample of the sized material was packed in a tubular flow reactor to demonstrate its effectiveness for promoting the removal of dissolved oxygen from a molecular oxygen-saturated (about 8.6 ppm $O_2$) aqueous stream further containing on the order of 0.1 weight percent methanol. The effluent from the tubular reactor was monitored continuously for dissolved oxygen with a dissolved oxygen probe assembly. The water was pumped through the flow system at a rate in the range of about 4 to 10 mL/min.

The dissolved oxygen level in the effluent was maintained at a low value over an extended time period clearly verifying the long-term effectiveness of the immobilized alcohol oxidase enzyme. For example, during a period of about 10 days the dissolved oxygen level was maintained at about 0.5 ppm dissolved oxygen in 83,735 mL of effluent.

The process was then discontinued for several days. The immobilized enzyme packing of my invention remained active for promoting the removal of dissolved oxygen from the water-methanol stream after resumption of the procedure. The dissolved oxygen level in the reactor effluent on resumption of water flow was maintained at about 0.5 ppm oxygen over a period of about 10 days with an additional throughput of approximately 66,600 mL. This run demonstrates that the procedure could be interrupted and successfully resumed, and that the immobilized enzyme retains its activity.

EXAMPLE II

This comparative run demonstrates the preparation of an immobilized sample of alcohol oxidase by contacting an aqueous iron(III) nitrate solution with cell-free supernatant ("PHS") in a pH range of 6 to 7.

The immobilization procedure was essentially the same as that described in Example I except that a 25 mL sample of PHS (containing 0.02 weight percent $NaN_3$ preservative; total activity 5463 eu) was treated with an aqueous ferric nitrate solution prepared by dissolving 5 g $Fe(NO_3)_3.9H_2O$ in 50 ml $H_2O$ (12.4 mmoles $Fe^{+3}$). The hydrous precipitate was isolated by suction filtration, washed four times with 200 mL portions of deionized water and air-dried.

The air-dried product exhibited slow but positive alcohol oxidase activity in a conventional dye-peroxidase assay test, specifically an o-dianisidine buffered dye and horse-radish peroxidase, but was brittle and could not be used satisfactorily or efficiently.

EXAMPLE III

This comparative run demonstrates the preparation of an immobilized sample of alcohol oxidase prepared from an aqueous zinc sulfate solution admixed with cell-free supernatant ("PHS") in the pH range of 6.4 to 6.6.

The immobilization procedure was essentially the same as that described in Example I except that a 47 mL sample of PHS (containing 0.02 weight percent $NaN_3$ preservative; total activity 10,598 eu) was treated with an aqueous zinc sulfate solution prepared by dissolving 10 g $ZnSO_4.7H_2O$ in 100 mL $H_2O$ (34.8 mmoles $Zn^{+2}$). The resulting hydrous precipitate was isolated by suction filtration, washed seven times with 250 mL portions of deionized water and air-dried. The filtrate from these washings showed no alcohol oxidase activity.

The air-dried product exhibited only nominal alcohol oxidase activity in the dye-peroxidase assay test (e.g., o-dianisidine buffered dye and horse-radish peroxidase). A slight level of activity was detectable by color change after the immobilized sample had been in contact with the assay solution for about 2 hours. This run demonstrates that a hydrous zinc gel is unsuitable for protein adsorption.

EXAMPLE IV

This run is essentially identical with that described in Example I except for the use of smaller amounts of reagents.

A 60 mL sample of PHS (containing 0.02 weight percent $NaN_3$ preservative; total activity about 20,000 eu) was treated with 60 mL of an aqueous solution prepared by dissolving 11.25 g $Al(NO_3)_3.9H_2O$ in 100 mL of $H_2O$ (30 mmoles $Al^{+3}$) in the pH range of 6.5 to 7.1. The resulting precipitate was isolated by suction filtration, washed five times with 250 mL portions of deionized water and air-dried. The initial filtrate exhibited 0.5 eu/mL activity in the dye-peroxidase assay test whereas no alcohol oxidase activity was detectable in the washings.

The 8 g of air-dried product was sized by selecting material which passed a #10 mesh but not a #20 mesh. A 5 g sample of this sized sample was packed in a tubular flow reactor to verify its activity to promote the removal of dissolved oxygen from a water stream spiked with 0.1 weight percent methanol. The flow-reactor results indicated that the immobilized enzyme system retained good activity over the period of four days.

EXAMPLE V

This run describes the preparation of an immobilized invertase by contacting an aqueous solution of aluminum nitrate with an aqueous solution of invertase in the pH range of 5.2 to 6.0. The procedure was similar to that described in Example I.

A solution of invertase in sodium acetate buffer at pH 5.0 (123.2 eu/mL) was treated with a solution prepared by dissolving 7.2 g $Al(NO_3)_3.9H_2O$ in 60 mL of water (19.2 mmoles $Al^{+3}$) in the pH range of 5.2 to 6.0. The resulting precipitate was removed by suction filtration to recover the immobilized invertase as a paste which weighed 8.9 grams. Assay of this product verified that its activity as a 50 milligram sample caused the production of 1.42 millimoles of glucose in a 1 mL aliquot of a 2 weight percent aqueous sucrose solution.

The paste was dried in a vacuum dessicator, first under refrigeration, and then at room temperature. The dried composite showed very high effective activity when tested on 2 percent aqueous sucrose solution, with 50 mg, 20 mg, and 7 mg of dried composite, each producing 1.2–1.3 mmoles of glucose per 1 mL of 2 weight percent aqueous sucrose solution.

EXAMPLE IV

This run demonstrates the preparation of an immobilized sample of alcohol oxidase-containing yeast cells by contacting the aqueous cell suspension with an aqueous solution of aluminum nitrate in the pH range of about 6 to 7. The technique used was essentially the same as that described in Example I.

A 50 mL suspension of *Pichia pastoris* yeast cells was treated with a solution prepared by dissolving 15 g of $Al(NO_3)_3 \cdot 9H_2O$ in 125 mL of water (40 mmoles $Al^{+3}$). The resulting precipitate of gel/cells was separated by suction filtration, washed twice with 250 mL portions of deionized water and air-dried to give 9.99 grams of product. The air-dried gel/cells product gave a slow positive assay test in the dye-peroxidase procedure. The slow response presumably was because the alcohol had to diffuse through the cell walls to come in contact with the alcohol oxidase. The presence of active catalase in the preparation was verified by placing a small portion of the air-dried sample in aqueous hydrogen peroxide. The evolution of gas, presumably $O_2$, signaled the catalase promotion of the reaction: $2H_2O_2 \rightarrow 2H_2O + O_2$.

EXAMPLE VII

These runs demonstrate the relative amounts of aluminum nitrate and "PHS" ("Pichia homogenate supenatant") to be contacted in order to minimize the residual enzyme activity in the filtrate washings of the immobilized enzyme system. Results are summarized in Table I:

TABLE I

Relative Amounts of PHS* and $Al^{+3}$ to Minimize Enzyme Activity in Filtrate Washings

| Run No. | Ratio mL PHS/g $Al(NO_3)_3 \cdot 9H_2O$ | Ratio$^a$ eu/mmole $Al^{+3}$ | Alcohol-Oxidase$^b$ eu/mL | Catalase$^c$ eu/mL |
|---|---|---|---|---|
| 7 | 20:1 (25/1.25) | 1794 | 9.04 | 25 |
| 8 | 15:1 (25/1.67) | 1344 | 0.334 | 2.78 |
| 9 | 12:1 (25/2.08) | 1077 | 0.174 | 2.72 |
| 10 | 10:1 (25/2.5) | 897 | 0.0 | 2.35 |
| 11 | 8:1 (25/3.125) | 718 | 0.0 | 1.12 |

*PHS represents "Pichia homogenate supernatant"; alcohol oxidase activity was 239.2 eu/mL; catalase activity was 3142 eu/mL.
$^a$A 25 mL sample of PHS was used in each run (total alcohol oxidase activity was 5,980 eu and total catalase activity was 78,550 eu).
$^b$These values indicate the approximate activity of alcohol oxidase in the filtrate washings of the immobilized enzyme preparation.
$^c$These values indicate the approximate activity of catalase in the filtrate washings of the immobilized enzyme preparation.

Referring to the results in Table I, the enzyme activity in the filtrate washings of the immobilized enzyme system approached zero as the ratio of initial total enzyme activity (eu) to added mmoles of $Al^{+3}$ enters the range of about 1000:1. As the ratio of eu/mmole $Al^{-3}$ becomes larger than about 1344 (Run 8), there appeared to be a sharp upturn in the filtrate enzyme activity, e.g., an increase from 0.334 eu/mL filtrate to 9.04 eu/mL filtrate. It is interesting to note that in the run in Example I which yielded an effective immobilized sample, that the ratio of eu in the PHS sample to mmoles of $Al^{+3}$ was of the order of 950:1 (167,000 eu ÷ 176 mmoles $Al^{+3}$). This ratio was in the range shown in Runs 9 and 10 of Table I wherein the enzyme activity of the filtrate washings became approximately zero.

The disclosure, including data, has illustrated the value and effectiveness of my invention. The examples, the knowledge and background of the field of the invention and the general principles of chemistry and of other applicable sciences have formed the bases from which the broad descriptions of my invention including the ranges of conditions and the generic groups of operable components have been developed, and formed the bases for my claims here appended.

I claim:

1. A process for the production of a dried immobilized gel/protein composite, which comprises:
   (A) substantially simultaneously admixing (a) an aqueous solution/dispersion of a physiologically and chemically active protein, (b) an aqueous solution of a Group IIIA metal salt selected from the group consisting of salts of gallium and indium, and (c) an alkaline solution, in proportions effective to coprecipitate said protein and said Group IIIA metal as a hydrous gel suspension, said gel suspension containing at least a substantial proportion of said protein,
   (B) separating said hydrous gel/protein, and
   (C) drying said hydrous gel/protein, thereby forming said dried immobilized gel/protein composite.

2. The process according to claim 1 wherein said alkaline solution is an aqueous solution of a Group IA alkali metal or ammonium hydroxide.

3. The process according to claim 1 wherein said protein is an enzyme and said Group IIIA metal is gallium.

4. The process according to claim 3 wherein said enzyme is a *Pichia pastoris*-derived alcohol oxidase.

5. The process according to claim 3 wherein said enzyme is a catalase.

6. The process according to claim 1 wherein said protein is an enzyme and said Group IIIA metal is indium.

7. The process according to claim 6 wherein said enzyme is a *Pichia pastoris*-derived alcohol oxidase.

8. The process according to claim 6 wherein said enzyme is a catalase.

9. The process of claim 20 wherein said aqueous dispersion of protein is an aqueous dispersion of whole cells.

10. The process according to claim 2 wherein said Group IIIA metal salt is an acetate, nitrate, chloride, or bromide salt of gallium or of indium.

11. The process of claim 10 employing a 1 to 10 weight percent aqueous solution of said metal salt.

12. The process of claim 11 employing 0.1N to 1N solution of said Group IA alkali metal of ammonium hydroxide.

13. The process of claim 12 employing a 50 to 5000 eu/mL aqueous protein.

14. The process of claim 2 further comprising: (D) grinding said dried composite to a dried particulate composite.

15. A dried immobilized protein composite comprising a dispersed physiologically and chemically active protein in a dry gel matrix of an oxide/hydroxide of gallium or of indium.

16. The immobilized protein composite of claim 15 wherein the metal is gallium.

17. The immobilized protein composite of claim 16 wherein said protein is an enzyme.

18. The immobilized protein composite of claim 17 wherein said enzyme is an alcohol oxidase, catalase, or both.

19. The immobilized protein composite of claim 15 wherein the metal is indium.

20. The immobilized protein composite of claim 19 wherein said protein is an enzyme.

21. The immobilized protein composition of claim 20 wherein said enzyme is an alcohol oxidase, catalase, or both.

22. The immobilized protein composite of claim 16 wherein said proteins are whole cells.

23. The immobilized protein composite of claim 22 wherein said whole cells are a *Pichia pastoris*.

24. The immobilized protein composite of claim 24 wherein said proteins are whole cells.

25. The immobilized protein composite of claim 24 wherein said whole cells are a *Pichia pastoris*.

* * * * *

UNITED STATES PATENT AND TRADEMARK OFFICE
CERTIFICATE OF CORRECTION

PATENT NO. : 4,551,431
DATED : Nov. 5, 1985
INVENTOR(S) : Phyllis J. Pierce

It is certified that error appears in the above-identified patent and that said Letters Patent is hereby corrected as shown below:

Col. 10, line 27: delete "20" and substitute --- 2 --- therefor.

Col. 10, line 64: delete "24" and substitute --- 19 --- therefor.

Signed and Sealed this

Sixteenth Day of December, 1986

*Attest:*

DONALD J. QUIGG

*Attesting Officer*    *Commissioner of Patents and Trademarks*